(12) United States Patent
Woerne

(10) Patent No.: US 11,844,680 B2
(45) Date of Patent: Dec. 19, 2023

(54) EXPANDABLE VASCULAR IMPLANT

(71) Applicant: JOTEC GmbH, Hechingen (DE)

(72) Inventor: Christian Woerne, Ostfildern (DE)

(73) Assignee: JOTEC GmbH, Hechingen (DE)

( * ) Notice: Subject to any disclaimer, the term of this patent is extended or adjusted under 35 U.S.C. 154(b) by 0 days.

(21) Appl. No.: 16/833,145

(22) Filed: Mar. 27, 2020

(65) Prior Publication Data

US 2020/0222215 A1 Jul. 16, 2020

Related U.S. Application Data

(63) Continuation of application No. PCT/EP2018/077595, filed on Oct. 10, 2018.

(30) Foreign Application Priority Data

Oct. 10, 2017 (DE) .................... 10 2017 123 461.6

(51) Int. Cl.
*A61F 2/856* (2013.01)
*A61F 2/962* (2013.01)
(Continued)

(52) U.S. Cl.
CPC .............. *A61F 2/07* (2013.01); *A61F 2/856* (2013.01); *A61F 2/90* (2013.01); *A61F 2/962* (2013.01);
(Continued)

(58) Field of Classification Search
CPC ............... A61F 2002/061; A61F 2/064; A61F 2002/068; A61F 2/07; A61F 2002/825;
(Continued)

(56) References Cited

U.S. PATENT DOCUMENTS 5,485,667 A * 1/1996 Kleshinski ........ A61M 25/0009
29/447
5,735,859 A * 4/1998 Fischell .................... A61F 2/95
606/108
(Continued)

FOREIGN PATENT DOCUMENTS

DE 102014116012 A1 * 5/2016 ............... A61F 2/07
WO WO 03/063729 8/2003

OTHER PUBLICATIONS

International Preliminary Report on Patentability for International Application No. PCT/EP2018/077595, dated Apr. 23, 2020.
(Continued)

*Primary Examiner* — Paul B Prebilic
(74) *Attorney, Agent, or Firm* — Jason H. Vick; Sheridan Ross, PC

(57) ABSTRACT

The invention relates to an expandable vascular implant for implantation into vessels of a patient, the vascular implant being convertible from a compressed state to an expanded state, and the vascular implant comprising the following: a hollow cylindrical main body having a longitudinal direction and a proximal end and a distal end, and a main body lumen which extends from the proximal to the distal end. The hollow cylindrical main body is formed by a tubular lattice structure, the tubular lattice structure having at least one first and at least one second region, the first region being fixedly connected to the second region, the first region being designed to be self-expandable, and the second region is designed to be balloon-dilatable.

17 Claims, 2 Drawing Sheets

(51) Int. Cl.
*A61F 2/90* (2013.01)
*A61F 2/07* (2013.01)
*A61F 2/966* (2013.01)
*A61F 2/958* (2013.01)

(52) U.S. Cl.
CPC ...... *A61F 2/966* (2013.01); *A61F 2002/9583* (2013.01); *A61F 2250/0048* (2013.01); *A61F 2250/0098* (2013.01)

(58) Field of Classification Search
CPC .......... A61F 2002/826; A61F 2002/828; A61F 2/856; A61F 2/90; A61F 2/954; A61F 2/958; A61F 2/962; A61F 2/966; A61F 2002/9583; A61F 2230/0069; A61F 2250/0048; A61F 2250/001; A61F 2250/0039
See application file for complete search history.

(56) References Cited

U.S. PATENT DOCUMENTS

| | | | |
|---|---|---|---|
| 11,471,278 B2* | 10/2022 | Braile | A61F 2/2418 |
| 2002/0007102 A1 | 1/2002 | Salmon et al. | |
| 2003/0105516 A1 | 6/2003 | Austin | |
| 2003/0176913 A1* | 9/2003 | Lenz | A61F 2/915 |
| | | | 623/1.15 |
| 2003/0195609 A1 | 10/2003 | Berenstein et al. | |
| 2005/0004647 A1* | 1/2005 | Bassoe | A61F 2/958 |
| | | | 623/1.11 |
| 2005/0131519 A1 | 6/2005 | Hartley | |
| 2013/0144373 A1 | 6/2013 | Shahriari | |
| 2013/0166010 A1* | 6/2013 | Vad | A61F 2/89 |
| | | | 623/1.2 |
| 2017/0014248 A1 | 1/2017 | Kelly | |
| 2017/0105834 A1 | 4/2017 | Dickinson et al. | |
| 2018/0125501 A1* | 5/2018 | Aboytes | A61B 17/1214 |
| 2019/0125517 A1* | 5/2019 | Cully | A61F 2/07 |

OTHER PUBLICATIONS

International Search Report for International Application No. PCT/EP2018/077595, dated Jan. 18, 2019.
Written Opinion for International Application No. PCT/EP2018/077595, dated Jan. 18, 2019.

* cited by examiner

EXPANDABLE VASCULAR IMPLANT

CROSS REFERENCES TO RELATED APPLICATIONS

This application is a continuation of international patent application PCT/EP2018/077595, filed on Oct. 10, 2018, designating the U.S., which international patent application has been published in German language and claims priority from German patent application DE 10 2017 123 461.6, filed on Oct. 10, 2017. The entire contents of these priority applications are incorporated herein by reference.

BACKGROUND

The present invention relates to an expandable vascular implant for implantation into vessels of a patient, the vascular implant being convertible from a compressed state into an expanded state.

Vascular implants are known in the prior art and are generally implanted in order to keep vessels open, especially blood vessels, and in order to treat aneurysms in arteries. According to the prior art, such vascular implants are also known as vascular stents/stent grafts.

An aneurysm is understood here to mean a distension or sacculation of an arterial blood vessel due to wall changes that are congenital or acquired. This sacculation can encompass the vascular wall as a whole or, as in the case of a so-called false aneurysm or so-called dissection, blood enters between the layers of the vascular wall from the lumen of the vessel and shears them apart. The nontreatment of an aneurysm can, in the advanced stage, lead to a rupture of the artery, with the consequence that the patient bleeds to death internally. To treat aneurysms or to treat vessels at threat of closure, the affected vessel is therefore stabilized by implantation of a vascular stent/stent graft in order to avoid a rupture of the vessel or to ensure generally that the vessel is kept open.

A relatively severe blockage of the blood vessels of affected patients can also lead to hypertension, ischemic injury, stroke or to a myocardial infarction. Arteriosclerotic lesions, which restrict or block coronary blood flow, are the main cause of ischemic heart disease.

These vascular stents/stent grafts used to keep vessels open or to treat aneurysms generally consist of a tubular metal frame, the lateral surface of which can be covered by a textile film or polymer film, thereby yielding a hollow cylindrical body. For implantation, the stent can be radially compressed—for example by means of a sheath which surrounds and compresses the stent—with the result that its cross-sectional area is distinctly reduced. Alternatively, for implantation, the stent can be applied to a dilation body, by means of which the stent can be expanded as required. Thus, with the aid of an insertion system, the stent/stent graft is brought into the region of the site to be treated or of the aneurysm, where the stent is released. Owing to the spring action of the metal frame or to the dilation of the dilation body, the stent expands and, while doing so, stretches its lateral surface, which becomes stuck internally in the blood vessel proximally and distally to the aneurysm or to the site to be kept open. In this way, the blood now flows through the stent/stent graft, and this thereby prevents further stress on the distension and ensures that the vessel is kept open.

In the prior art, a great many of these expandable catheters are known. A very wide variety of different stents are used depending on the type of application. A distinction is made here between balloon-dilatable and self-expandable systems. The self-expandable properties arise from the use of self-expanding materials, such as, for example, nitinol. Balloon-dilatable systems are expanded by a force exerted from within when the system is, for example, mounted on a balloon.

In the case of the dilation of balloon catheters by means of a dilation body, the metal frame of the balloon catheter is dilated by the dilation of the dilation balloon which is inserted from within into the metal frame. The balloon catheters are generally placed into the stenosis from the groin via a guide wire and guide catheter and inflated by pressure. As a result, the site of narrowing is eliminated and an operation is avoided. One disadvantage of a balloon-dilatable stent is that it must be protected from damage during insertion. Damage to the dilation body would mean that it cannot be dilated at the desired site. In contrast to self-expandable stents, balloon-dilatable stents are easy-to-handle and precisely placeable. Another disadvantage of balloon-dilatable stents is the stretching of the layers of the vascular wall by a balloon, meaning that, for example, the endothelial cell layer can be destroyed as a result of the dilation of the balloon-dilatable stent even at slight unfolding pressures 3 bar). What usually occurs disadvantageously as a result is an activation of coagulation. Balloon-dilatable stents can be present in a covered or uncovered state.

Another stent known in the prior art is the so-called covered self-expandable stent. This is a vascular support or a medical implant in the form of a small lattice structure in tube form composed of metal fibers or plastic fibers. In the case of a covered stent, the meshes of the lattice structure are predominantly covered by an implant material; this creates a tubular structure (a stent graft) consisting of an implant material, which tubular structure is supported by a (metal) scaffold, the stent part. The expansion of the metal frame is brought about especially through the use of self-expanding metal, such as, for example, nitinol. Self-expandable stent grafts are highly flexible and radially elastic. However, placement of such a stent requires much experience in the implantation of such a stent.

It is therefore an object of the present invention to provide an expandable vascular implant which can overcome the above-described disadvantages.

SUMMARY

According to the invention, this object is achieved by an expandable vascular implant for implantation into vessels of a patient, the vascular implant being convertible from a compressed state into an expanded state, the vascular implant comprising the following: a hollow cylindrical main body having a longitudinal direction and having a proximal and a distal end, and having a main body lumen extending from the proximal up to the distal end, the hollow cylindrical main body being formed by a tubular lattice structure, wherein the tubular lattice structure comprises at least one first and at least one second region, the first region being firmly connected to the second region and the first region being self-expandable and the second region being balloon-dilatable.

The object underlying the invention is furthermore achieved by an insertion system for release and for expansion of an expandable vascular implant, the insertion system comprising a retraction sheath for compression of at least the first region of the vascular implant, and also a first catheter having a dilation body.

The object underlying the invention is furthermore achieved by the use of an insertion system for insertion and release of an expandable vascular implant into vessels of a patient for treating a vasoconstriction or rupture of a vessel.

Furthermore, the object underlying the invention is also achieved by a method for releasing an expandable vascular implant into vessels of a patient for treating a vasoconstriction or rupture of a vessel, the method comprising the following steps:
a) providing an insertion system comprising a vascular implant for release and expansion of a vascular implant for implantation into vessels of a patient;
b) inserting the insertion system loaded with the expandable vascular implant up to the site to be treated in the vessel; and
c) releasing the expandable vascular implant by dilation of the dilation body and withdrawal of the retraction sheath.

The object underlying the invention is completely achieved in this manner.

What is provided by the expandable vascular implant according to the invention is a vascular implant which can be used for supporting unstable, fragile or thrombic vascular walls and especially for treating aneurysmal vessels. This is achieved by the specific construction of the vascular implant, which is based on a hollow cylindrical main body composed of a first self-expandable region and a second balloon-dilatable region, the two regions being firmly connected to one another and forming the tubular lattice structure together.

The term "expandable" is understood here to encompass both the self-expandable and the balloon-dilatable properties of the vascular implant according to the invention. The expandable vascular implant according to the invention comprises both self-expandable and balloon-dilatable regions; in short, this invention thus uses the term "expandable" vascular implant because the two regions can be self-expanded or be dilated by means of a balloon. Furthermore, the term "expansion" is understood to mean both the self-expanding expansion and the balloon-dilating dilation.

What is thus possible with the expandable vascular implant according to the invention is that, in particular, the expandable vascular implant to be used can be used for treating those vessels in which both a self-expandable stent and a balloon-dilatable stent are to be used out of necessity. What is particularly advantageous here is that there is no need to use two stents one directly after another, in the form of two procedures, but just one vascular implant. Particularly advantageously, this means that only one procedure is performed.

Fundamentally, the terms "distal" and "proximal" are used to refer to the respective ends of vascular implants, the term "distal" referring to the part or the end that is further downstream with regard to the bloodstream. By contrast, the term "proximal" refers, again with regard to the bloodstream, to a part or the end that is further upstream with regard to the bloodstream. In other words, the term "distal" means in the direction of the bloodstream, and the term "proximal" means opposite to the direction of the bloodstream. By contrast, in the case of catheters or insertion systems, the term "distal" refers to the end of the catheter or insertion system that is inserted into the patient, or that is furthest away from the user's perspective, and the term "proximal" refers to the end that is nearer to the user.

What is meant here by "hollow cylindrical main body" is the main body of the expandable vascular implant that comprises the tubular lattice structure. Furthermore, the hollow cylindrical main body can optionally comprise prosthesis material. The "tubular lattice structure" is, in turn, made up of stent springs which are either held together via prosthesis material, or form a hollow cylindrical main body because of their construction, for example because they are meshed or formed as a braided structure.

What is made possible by the construction of the expandable vascular implant according to the invention is that individual vascular implants matched with individual patients to be treated or vessels to be treated can be made. Here, it is especially useful to be able to produce made-to-measure stent grafts with regard to the anatomy of the specific vessel. Furthermore, the expandable vascular implant according to the invention can also be prefabricated as a universally usable vascular implant.

According to the invention, the tubular lattice structure serves not only to give the expandable vascular implant the necessary structure, but also to press the expandable vascular implant against the vascular wall when implanted and to thus keep the vascular implant in position in the vessel. The material properties of the tubular lattice structure are dependent on the vessel to be treated, and dependent on the first and second region. For example, in the case of a vessel with a very thin wall, it is advantageous to use materials which are less rigid. Furthermore, the tubular lattice structure of the first region is preferably formed from a self-expandable material, whereas the tubular lattice structure of the second region is preferably formed from a balloon-dilatable material which can deform by means of an applied force.

According to the invention, the expandable vascular implant can be present as a completely "covered", partially "covered" or "uncovered" vascular implant. In the case of the covered or partially covered vascular implant, the tubular lattice structure is covered by a textile film or polymer film, thereby yielding a hollow cylindrical body. The tubular lattice structure is preferably formed as a wire braid, or from so-called stent springs that are meanderingly encircling and are arranged one after another, which stent springs are optionally connected to one another via supporting struts made of wire or which stent springs are merely connected to one another via the prosthesis material. The biocompatibility of the materials used means that the contact between the expanded vascular implant and the vascular wall is free of complications.

In one embodiment of the vascular implant according to the invention, the tubular lattice structure of the first and/or the second region at least partially comprises a prosthesis material.

Said embodiment is thus a so-called "covered" vascular implant consisting of the tubular lattice structure and an at least partially covering graft material. In this design, the lattice structure can be present as individual springs which are introduced or sewn in the graft material, or as a meshed or braided lattice structure which is connected to the prosthesis material. According to the invention, the lattice structure can lie within the hollow cylindrical main body, meaning that the prosthesis material surrounds the hollow cylindrical main body, or vice versa.

This design offers the advantage that the prosthesis material prevents blood, or constituents of blood or deposits, from passing through the wall of the stent graft and prevents tissue from growing through the wall into the interior of the stent graft. Thus, the pressure on the vascular wall at the implantation site of the vascular implant is relieved and possible embolisms at these sites are prevented.

Such vascular implants can, for example, be used in aneurysms. In this case, they seal the vessel in the region of the site to be treated and thus bridge the blood flow within the vessel.

In one embodiment of this invention, only one of the first and second regions can comprise the prosthesis material, whereas the other region is, for example, formed as a meshed or braided latticed structure. In a further preferred embodiment of a covered vascular implant, the vascular implant is virtually completely covered by the prosthesis material. In this case, both the first and the second region of the vascular implant thus comprise a prosthesis material fastened together with the lattice structure. At the same time, it is evident that free latticed ends for anchoring in the vessel can be comprised by the latticed structure arising in each case, i.e., the outermost proximal end and the outermost distal end. In a further embodiment, both regions can merely partially comprise a prosthesis material.

In a further embodiment, the tubular latticed structure of the first region is formed from a self-expandable material, especially from nitinol, and the tubular latticed structure of the second region is formed from a balloon-dilatable material, especially from a cobalt-chromium-containing alloy.

The self-expandable material of the first region is preferably a metal or a metal alloy, especially a metallic shape-memory alloy, for example nitinol (a nickel-titanium alloy), Elgiloy®, Phynox®, MP35N, stainless steel, cobalt alloy or titanium alloy. Alternatively, the self-expandable material can also be formed as another biocompatible material, such as, for example, plastic or monofilament and/or multifilament and/or composite glass fibers. These materials can be converted from a compressed state into a relaxed state by themselves. The self-expandable material can also be formed from biodegradable materials.

The balloon-dilatable material of the second region is preferably an elastic material which can be distended with the aid of an expandable dilation body. Possible materials are, for example, a polymeric or a metallic material such as metal alloys, steel, stainless steel, tantalum, nickel alloys, titanium alloys, cobalt alloys or cobalt-chromium alloys. These materials are deformable, meaning that the tubular lattice structure is convertible from a nonexpanded state into a balloon-dilated state by an applied force.

In one embodiment of the present invention, at least two, three or four first regions and/or at least two, three or four second regions which are arranged one after another and in a mutually alternating manner in the longitudinal direction are provided.

Said embodiment offers the advantage that a vascular implant which can be adapted for the individual needs of vessels is provided. Depending on the vessel, what may be required is that both self-expandable and balloon-dilatable vascular implants are to be used one after another. In the prior art, it would be necessary here to introduce multiple successive vascular implants into the vessel, and this is, in turn, associated with multiple procedures. A reliable fixation of multiple successive vascular implants requires much experience and frequently leads to undesired complications. According to the invention, this is achieved by a vascular implant comprising various regions. As a result, the introduction of multiple stents is replaced with merely one vascular implant.

A person skilled in the art will be able to determine the specific number of the first region and of the second region on the basis of the present teaching and in consideration of the vascular implant to be used and the particular vascular anatomy of a patient that is under consideration.

In a further embodiment, the vascular implant comprises, in the first and/or in the second region, at least one side branch that branches off.

Depending on the vascular anatomy, it may be the case that a side arm of the vessel branches off in the region in which the vascular implant is to be introduced. This would be cut off from being supplied, if the vascular implant were not to have a side branch in this position. Thus, what is provided is a vascular implant which is also used in vessels comprising further vessels that branch off.

Advantageously, the vascular implant according to the invention is formed such that side branches that branch off can also be bridged by the vascular implant. What is advantageously brought about as a result is that the region around the side branch can also be provided with a stent, which region is, because of its thin wall, more sensitive than the section of the side vessel that is immediately situated at the branch-off point from a main vessel and is made of a thicker wall. Therefore, this embodiment offers the advantage that it can be adapted to the particular anatomical circumstances of the patient to be treated.

In a further embodiment, a marker containing a radiopaque material or completely consisting of radiopaque material is situated on the vascular implant, the marker being situated especially at the ends and/or between the first and the second region.

With the aid of the markers situated on specific sites of the vascular implant, it is possible to accurately determine in a particularly rapid manner the position of the vascular implant during and after implantation. Suitable as specific sites for this purpose are, in particular, the junctions between the first and second region and also the ends of the vascular implant. If the vascular implant comprises a side branch that branches off, the markers can serve to ensure the correct positioning of the vascular implant with regard to the side arm.

In a further preferred embodiment of the vascular implant, the vascular implant has a diameter in the expanded state between 5 and 50 mm, especially between 15 and 50 mm, especially 5 mm, 6 mm, 7 mm, 8 mm, 9 mm, 10 mm, 11 mm, 12 mm, 13 mm, 14 mm, 15 mm, 20 mm, 25 mm, 30 mm, 35 mm, 40 mm or 50 mm.

Said embodiment can provide many different suitable vascular implants, depending on the vascular anatomy. A vascular implant according to the invention can be provided not only for small vessels, but also for larger vessels having a diameter of 15 mm.

In a further embodiment of the vascular implant, the vascular implant has a different diameter in the first and in the second region.

In this case, it is possible not only to make individual vascular implants matched with individual patients to be treated, but also, on the other hand, to prefabricate universally usable vascular implants.

In a further preferred embodiment, the vascular implant has a length of from 30 mm to 250 mm, especially from 100 to 250, especially 30 mm, 40 mm, 50 mm, 60 mm, 70 mm, 75 mm, 80 mm, 90 mm, 100 mm, 125 mm, 150 mm, 170 mm, 200 mm, 230 mm or 250 mm.

On the basis of said embodiment, it is possible to ensure that vascular implants of different lengths can be produced. The first region can have the same length or a different length compared to the second region; length can be adapted to the vessel, depending on the nature of the vessel. The first region can thus account for, for example, 5% to 95% of the entire vascular implant, with the second region being able to be respectively present within the range from 5% to 95%. Here, the percentages are based on the total length of the vascular implant which is formed from a first and a second region, meaning that the sum of the first and second region yields 100%.

As already mentioned at the start, the present invention also relates to an insertion system for release and for expansion of an expandable vascular implant, the insertion system comprising a retraction sheath for compression of at least the first region of the vascular implant, and also a first catheter having a dilation body.

By means of said insertion system, the above-described vascular implant can be inserted into a vessel and expanded at the desired site in a reliable manner.

According to the invention, the second region, which is balloon-dilatable, is dilated by the dilation body and the dilation thereof. The dilation body and optionally any balloon segments which the dilation body may have can, for example, be dilated by a fluid or gas that is introduced. Here, the dilation body is situated within the vascular implant, meaning that the vascular implant, especially the second region, rests on the dilation body. The material of which the balloon segments of the catheter according to the invention consist, or comprise such a material, is preferably a polymer and, for example, selected from the group comprising polyurethane, polyether polyurethane, polyethylene terephthalate polybutylene terephthalate polyamide and also copolymers and mixtures thereof.

Furthermore, the insertion system comprises a retraction sheath which can compress at least the first region of the vascular implant and can be withdrawn at the desired site, with the result that the first region of the vascular implant can self-expand. For this purpose, the retraction sheath has previously been pulled over at least the first region of the vascular implant for compression.

In a further design of the invention, the dilation body of the insertion system is dilatable by supply of a fluid.

In said design, the dilation body can be formed with balloon segments into which it is possible to supply a predetermined quantity of fluid. Here, the fluid can be a gas or a liquid, for example saline or a radiopaque contrast medium and any fluid usually used in this area for dilating dilation bodies.

In a further design of the invention, the first catheter is designed to support the vascular implant and dilate the second region.

The present invention relates furthermore to the use of an insertion system for insertion and release of an expandable vascular implant into vessels of a patient for treating a vasoconstriction or rupture of a vessel.

As already mentioned at the start, the present invention also relates to the method for releasing an expandable vascular implant into vessels of a patient for treating a vasoconstriction or rupture of a vessel.

In this connection, the vessel is preferably a blood vessel or some other hollow organ of a preferably human patient such as, for example, the bile duct or the urethra, too.

Further advantages and features are revealed by the following description and the attached drawing.

It is evident that the features stated above and the features yet to be elucidated below are usable not only in the various specified combinations, but also in other combinations or alone, without departing from the scope of the present invention.

BRIEF DESCRIPTION OF THE DRAWINGS

An exemplary embodiment of the invention is depicted in the drawing and is described in detail below with reference to said drawing.

EMBODIMENTS

Figure 1:
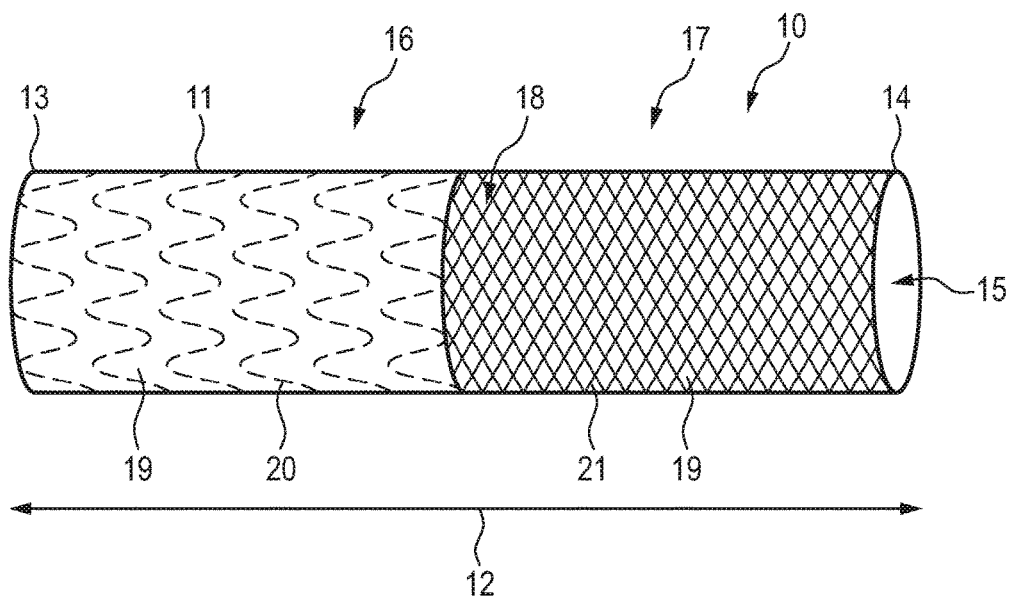
FIG. 1 shows a schematic representation, not true-to-scale, of a first embodiment of the expandable vascular implant according to the invention in the expanded state.

FIG. 1 shows a schematic representation, not true-to-scale, of a first embodiment of the expandable vascular implant 10 according to the invention for implantation into vessels of a patient in the expanded state. The vascular implant 10 is shown as a hollow cylindrical main body 11 having a longitudinal direction 12 and a first and second end 13, 14, and having a main body lumen 15 extending from the first end 13 up to the second end 14. The first and the second end 13, 14 correspond, respectively, to the proximal and the distal end 13', 14', or vice versa. Furthermore, the vascular implant 10 comprises a first and second region 16, 17. The first region 16, which is self-expandable, extends from the first end 13 up to the second region 17, which is firmly connected to the first region 16. The second region 17, which is balloon-dilatable, extends starting from the first region 16 up to the second end 14.

As can be gathered from FIG. 1, the hollow cylindrical main body 11 is formed by a tubular lattice structure 18 which is covered by a prosthesis material 19, or to which the lattice structure 18 is attached, for example sewn or adhesively bonded. In a further preferred embodiment, the vascular implant 10 only partially comprises a prosthesis material 19 or does not comprise a prosthesis material 19 (not shown). In this case, the vascular implant 10 can be covered by prosthesis material 19 to an extent of approx. 30%, 50% or 100%.

According to the invention, the lattice structure 18 of the vascular implant 10 can be formed from stent springs 20. Said stent springs 20 can be formed from meanderingly encircling sharp curves which are each formed from two legs with peaks or troughs in between, which are arranged one after another in the longitudinal direction 12. As shown in FIG. 1, the first self-expandable region 16 comprises such stent springs 20. These can also be connected to one another, with the result that a meshed structure or braided structure 21 is formed. In FIG. 1, the second balloon-dilatable region 17 has such a structure 21. The braided structure 21 arises by intersecting a multiplicity of filamentary elements in a plane perpendicular to the longitudinal direction 12 of the vascular implant 10 and at a braiding angle and forming meshes. The mesh density is higher in the expanded state than in the compressed state.

To form covered vascular implants 10, the stent springs 20 or the meshed structure or braided structure 21 can be connected on the outer side or inner side of the hollow cylindrical body 11 by means of a prosthesis material 19 attached to the stent springs 20 or to the meshed structure or braided structure 21.

The different properties of the lattice structure 18 in the first and the second region 16, 17 mean that said regions comprise a different material, or are formed from a different material. Whereas the material of the first region 16 is self-expandable, the material of the second region 17 is balloon-dilatable. The first region 16 can, for example, be sewed or adhesively bonded to the second region 17. In one embodiment, the two regions 16, 17 can be connected to one another via the prosthesis material 19. In particular, preference is given to connections of the kind in which the individual regions 16 and 17 are firmly connected to one another such that the two regions 16, 17 do not separate during implantation of the vascular implant 10.

Figure 2:
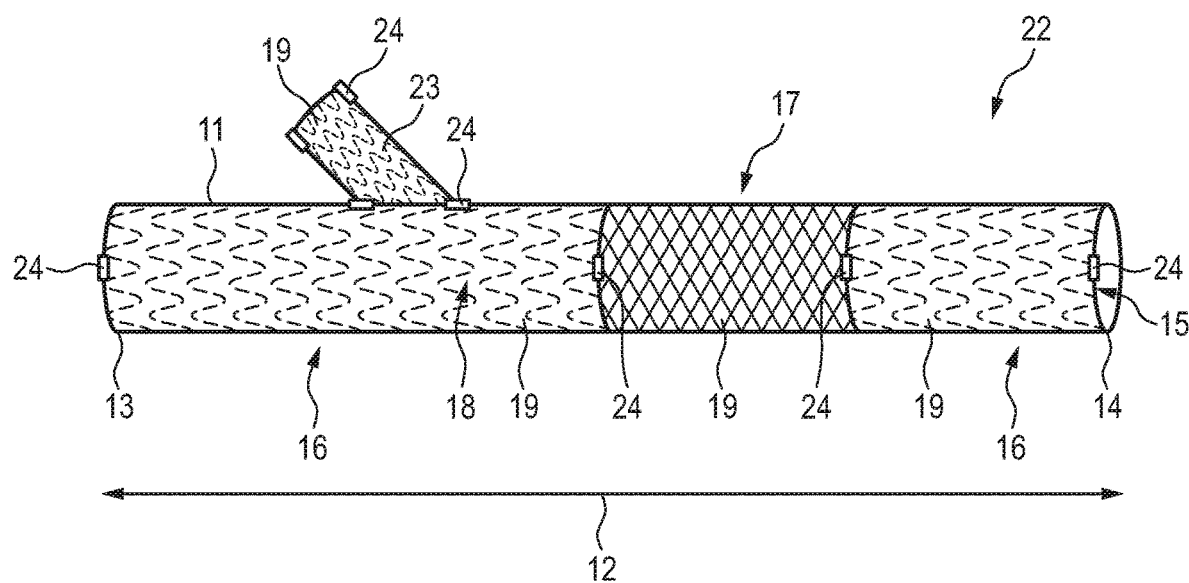
FIG. 2 shows a schematic representation, not true-to-scale, of a second embodiment of the expandable vascular implant according to the invention in the expanded state.

FIG. 2 shows a schematic representation, not true-to-scale, of a second embodiment of the expandable vascular implant 22 according to the invention in the expanded state, wherein the same features as those of the vascular implant 10 from FIG. 1 are provided with the same reference signs.

Accordingly, the vascular implant 22 also has a hollow cylindrical main body 11, and a longitudinal direction 12, a first and second end 13, 14, and a main body lumen 15 extending from the first end 13 up to the second end 14. Furthermore, the vascular implant 22 comprises two first regions 16 and one second region 17, with the second region 17 being surrounded by the two first regions 16. Here, the first region 16 extends from the first end 13 up to the second region 17 and the second first region 16 extends from the second region 17 up to the second end 14.

As can be gathered from FIG. 2, the hollow cylindrical main body 11 is formed by a tubular lattice structure 18, this being formed from two first regions 16 and one second region 17. Both the first region 16 and the second region 17 are covered by a prosthesis material 19, or to which the lattice structure 18 is attached, for example sewn or adhesively bonded. In a further preferred embodiment, the vascular implant 10 only partially comprises a prosthesis material 19 or does not comprise a prosthesis material 19 (not shown). In this case, the vascular implant 22 can be covered by prosthesis material 19 to an extent of approx. 30%, 50% or 100%.

Furthermore, the vascular implant 22 comprises a side branch 23 in the first region 16. This design allows the implantation of the vascular implant 22 into a vessel comprising vessels that branch off. For example, it is thus possible for the vascular implant 22 to bridge not only a main vessel, but also a secondary vessel. In this case, there is, for example, no blockage of the blood flow into the side vessel. In one embodiment not depicted, the side branch 23 can also be formed as fenestration, through which a further vascular implant can be placed in order to supply vessels that branch off.

In one embodiment not depicted, the vascular implant 22 can comprise further first or second regions 16, 17, wherein the regions mutually alternate.

Furthermore, the vascular implant 22, shown in FIG. 2, comprises numerous markers 24, depicted as rectangular boxes. Said marker 24 contains a radiopaque material or completely consists of a radiopaque material. When the vascular implant 22 is being implanted, said markers 24 make placement at a desired site in the vessel possible for the treating physician. The markers 24 are situated especially at the first and second end 13, 14, between the first and second region 16, 17 and/or at the side branch 23 that branches off. With the aid of the markers 24 situated on specific sites of the vascular implant 22, it is possible to accurately determine in a particularly rapid manner the position of the vascular implant 22 during and after implantation. Preferably, the radiopaque markers 24 are composed of one or more of the following materials, for example gold, palladium, tantalum, chromium, silver, etc.; in addition, the shape of the markers 24 can be as desired, for example round or angular, and/or have, for example, the shape of letters, numbers or figures, which are helpful for the orientation of the vascular implant 22 in the vessel.

Figure 3:
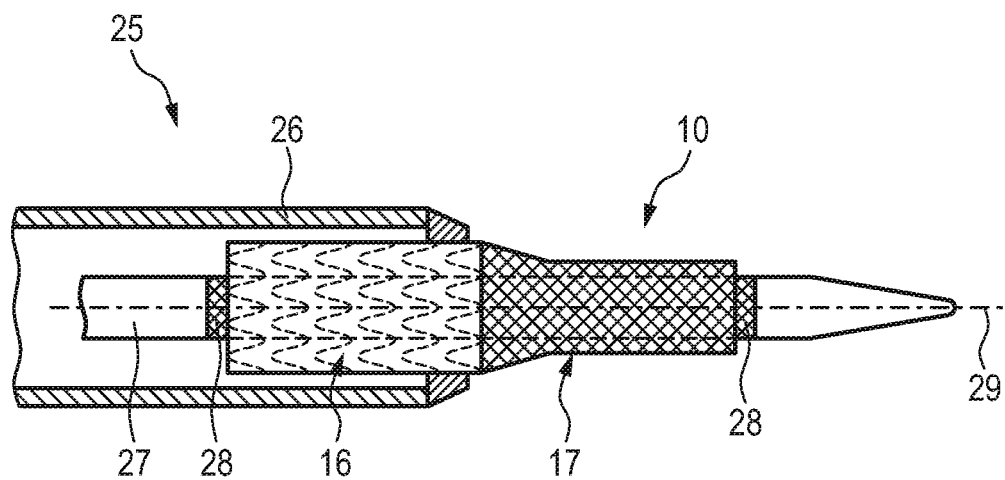
FIG. 3 shows a schematic representation, not true-to-scale, of a first embodiment of the insertion system for release and expansion of the expandable vascular implant together with the compressed vascular implant.
Figure 4:
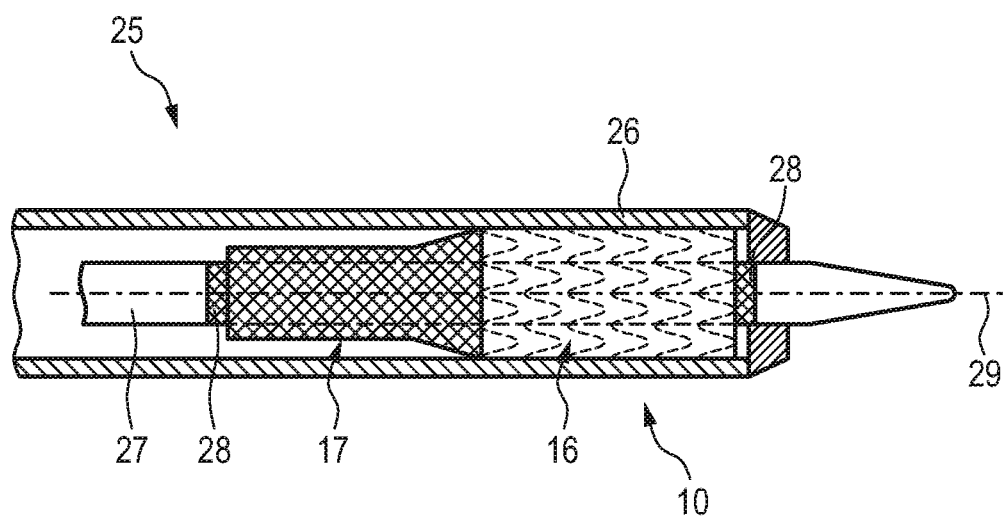
FIG. 4 shows a schematic representation, not true-to-scale, of a second embodiment of the insertion system for release and expansion of the expandable vascular implant together with the compressed vascular implant.

FIG. 3 and FIG. 4 respectively show a schematic depiction, not true-to-scale, of a first and second embodiment of the insertion system 25 for release and expansion of the expandable vascular implant 10 together with the compressed vascular implant 10.

The insertion system 25 comprises a retraction sheath 26 and a first catheter 27. The first catheter 27 is situated in the interior of the insertion system 25. The vascular implant 10 is situated such that it surrounds the catheter 27 or is pulled over the catheter 27. In the region of the catheter on which the second balloon-dilatable region 17 of the vascular implant 10 is situated, the catheter 27 preferably has a dilation body which, for example, can be filled with a fluid in order to dilate the second region 17 of the vascular implant 10. Situated around at least the first region 16 of the vascular implant 10 is the retraction sheath 26 of the insertion system 25. The retraction sheath 26 is formed such that it compresses the first region 16 and can, if the vascular implant 10 is situated at the desired site in the vessel, expand said region through withdrawal of the retraction sheath 26.

In addition to the vascular implant 10, the insertion system 25 can also comprise markers 28 consisting of radiopaque material or containing radiopaque material. Said markers 28 allow a reliable positioning of the vascular implant 10 within the vessel.

The insertion systems 25 in FIG. 3 and in FIG. 4 merely differ in the different orientation of the vascular implant 10 and thus in the different design of the insertion system 25. Whereas the second region 17, of the vascular implant 10 shown in FIG. 3, lies distally on the catheter 27, i.e., the end of the catheter 27 or insertion system 25 that is inserted into the patient, or that is furthest away from the user's perspective, the second region 17, of the vascular implant 10 shown in FIG. 4, is located proximally on the catheter 27, i.e., the end of the catheter 27 that is nearer to the user.

In this design, the retraction sheath 26, shown in FIG. 3, lies only partially over the vascular implant 10, whereas the retraction sheath 26, shown in FIG. 4, encases the entire vascular implant 10.

The insertion system 25 according to the invention is used by loading it with a vascular implant 10, the vascular implant 10 being in a compressed state. During implantation, the insertion system 25 is advanced to the desired site in the vessel, preferably via a guide wire 29. Here, the position can, for example, be ascertained with the aid of the markers 24 and 28. Once the vascular implant 10 is positioned at the desired site, the retraction sheath 26 is withdrawn and the balloon segment of the dilation body is dilated. Once the vascular implant 10 is expanded, the balloon segments of the dilation body are emptied and the catheter 27, together with the retraction sheath 26, are removed from the vessel, whereas the vascular implant 10 remains in the vessel.

What is claimed is:

1. An expandable vascular implant configured for implantation into vessels of a patient, the vascular implant being convertible from a compressed state into an expanded state, the vascular implant comprising:
   a hollow cylindrical main body having a longitudinal direction and having a proximal and a distal end, and having a main body lumen extending from the proximal up to the distal end, the hollow cylindrical main body being formed by a tubular lattice structure, wherein the tubular lattice structure comprises at least one first and at least one second region, the first and the second regions including different materials, the first region having a first diameter in an expanded state extending from the proximal end to the second region and being firmly connected to the second region, the first region formed from stent springs, the stent springs formed from meanderingly encircling sharp curves which are each formed from two legs with peaks or troughs in between, which are arranged one after another in the longitudinal direction, the first region further comprising a prosthesis material attached to the stent springs, the second region having a second diameter in an expanded state extending from the distal end to the first region, and the first region being self-expandable and the second region being balloon-dilatable, wherein the second region is constructed of a mesh with intersecting a multiplicity of filamentary elements in a plane perpendicular to the longitudinal direction of the vascular implant at a braiding angle and forming meshes, and wherein the vascular implant includes a marker that contains a radiopaque material, and the marker is provided at one or more of the ends and between the first and second region, wherein the radiopaque material of the marker is different from the material of the tubular lattice structure, or wherein the marker has a shape different from the tubular lattice structure.

2. The vascular implant as claimed in claim 1, wherein the tubular lattice structure of one or more of the first and the second region at least partially comprises a prosthesis material.

3. The vascular implant as claimed in claim 1, wherein the tubular lattice structure of the first region is formed from a self-expandable material and the tubular lattice structure of the second region is formed from a balloon-dilatable material.

4. The vascular implant as claimed in claim 1, further comprising at least two, three or four first regions and at least two, three or four second regions which are arranged one after another and in a mutually alternating manner in the longitudinal direction.

5. The vascular implant as claimed in claim 1, wherein in one or more of the first and the second region, at least one side branch branches off.

6. The vascular implant as claimed in claim 1, wherein the vascular implant has a diameter in the expanded state between 5 and 50 mm.

7. The vascular implant as claimed in claim 1, wherein the vascular implant has a different diameter in the first and in the second region.

8. The vascular implant as claimed in claim 1, wherein the vascular implant has a length of from 30 mm to 250 mm.

9. An insertion system for release and for expansion of an expandable vascular implant as claimed in claim 1, wherein the insertion system comprises a retraction sheath for compression of at least the first region of the vascular implant, and also a first catheter having a dilation body.

10. The insertion system as claimed in claim 9, wherein the dilation body is dilatable by supply of a fluid.

11. The insertion system as claimed in claim 9, wherein the first catheter is designed to support the vascular implant and dilate the second region.

12. A method for delivering and releasing an expandable vascular implant into a vessel of a patient in need thereof for treating a vasoconstriction or rupture of a vessel, the method comprising:
providing an expandable vascular implant including a hollow cylindrical main body having a longitudinal direction and having a proximal and a distal end, and having a main body lumen extending from the proximal up to the distal end, the hollow cylindrical main body being formed by a tubular lattice structure, wherein the tubular lattice structure comprises at least one first and at least one second region, the first and the second regions including different materials, the first region having a first diameter in an expanded state extending from the proximal end to the second region and being firmly connected to the second region, the first region formed from stent springs, the stent springs formed from meanderingly encircling sharp curves which are each formed from two legs with peaks or troughs in between, which are arranged one after another in the longitudinal direction, the first region further comprising a prosthesis material attached to the stent springs, the second region having a second diameter in an expanded state extending from the distal end to the first region, and the first region being self-expandable and the second region being balloon-dilatable, wherein the second region is constructed of a mesh with intersecting a multiplicity of filamentary elements in a plane perpendicular to the longitudinal direction of the vascular implant at a braiding angle and forming meshes, wherein the vascular implant includes a marker that contains a radiopaque material, and the marker is provided at one or more of the ends and between the first and second region, wherein the radiopaque material of the marker is different from the material of the tubular lattice structure, or wherein the marker has a shape different from the tubular lattice structure;
providing an insertion system comprising a retraction sheath for compression of at least the first region of the expandable vascular implant, and a first catheter having a dilation body, and loading the expandable vascular implant into the insertion system;
inserting the insertion system loaded with the expandable vascular implant up to a site to be treated in the vessel; and
releasing the expandable vascular implant by dilation of the dilation body and withdrawal of the retraction sheath.

13. The vascular implant as claimed in claim 1, wherein the tubular lattice structure of the first region is formed from a self-expandable material including nitinol, and the tubular lattice structure of the second region is formed from a balloon-dilatable material including a cobalt-chromium-containing alloy.

14. The vascular implant as claimed in claim 1, wherein the vascular implant has a diameter in the expanded state between 15 and 50 mm.

15. The vascular implant as claimed in claim 1, wherein the vascular implant has a diameter in the expanded state of 5 mm, 6 mm, 7 mm, 8 mm, 9 mm, 10 mm, 11 mm, 12 mm, 13 mm, 14 mm, 15 mm, 20 mm, 25 mm, 30 mm, 35 mm, 40 mm, 45 mm or 50 mm.

16. The vascular implant as claimed in claim 1, wherein the vascular implant has a length of from 100 mm to 250 mm.

17. The vascular implant as claimed in claim 1, wherein the vascular implant has a length of 30 mm, 40 mm, 50 mm, 60 mm, 70 mm, 75 mm, 80 mm, 90 mm, 100 mm, 125 mm, 150 mm, 170 mm, 200 mm, 230 mm or 250 mm.

* * * * *